(12) United States Patent
Zhang et al.

(10) Patent No.: US 9,682,920 B2
(45) Date of Patent: Jun. 20, 2017

(54) METHOD FOR PRODUCING 2-(4-N,N-DIALKYLAMINO-2-HYDROXYBENZOYL) BENZOATES

(71) Applicant: DSM IP ASSETS B.V., Heerlen (NL)

(72) Inventors: Ji-Yong Zhang, Basel (CH); Xu-Feng Xu, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/901,170

(22) PCT Filed: Jun. 25, 2014

(86) PCT No.: PCT/EP2014/063319
§ 371 (c)(1),
(2) Date: Dec. 28, 2015

(87) PCT Pub. No.: WO2014/207002
PCT Pub. Date: Dec. 31, 2014

(65) Prior Publication Data
US 2016/0152554 A1  Jun. 2, 2016

(30) Foreign Application Priority Data

Jun. 27, 2013 (WO) ................ PCT/CN2013/000772

(51) Int. Cl.
*C07C 227/18* (2006.01)
*C07C 227/40* (2006.01)
*C07D 295/033* (2006.01)
*C07D 209/02* (2006.01)

(52) U.S. Cl.
CPC .......... *C07C 227/18* (2013.01); *C07C 227/40* (2013.01); *C07D 209/02* (2013.01); *C07D 295/033* (2013.01)

(58) Field of Classification Search
CPC ... C07C 227/18; C07C 227/40; C07C 229/52; C07D 209/02; C07D 295/033
See application file for complete search history.

(56) References Cited

U.S. PATENT DOCUMENTS

| | | | |
|---|---|---|---|
| 6,409,995 B1 * | 6/2002 | Habeck | A61K 8/411 424/59 |
| 8,802,887 B2 * | 8/2014 | Champ | C07C 227/42 560/57 |
| 2005/0165099 A1 * | 7/2005 | Heidenfelder | C07C 229/52 514/539 |

FOREIGN PATENT DOCUMENTS

| | | |
|---|---|---|
| CN | 1653035 | 8/2005 |
| WO | WO 03/086340 | 10/2003 |
| WO | WO 03/097578 | 11/2003 |
| WO | WO 2004/052837 | 6/2004 |
| WO | WO 2008/135360 | 11/2008 |

OTHER PUBLICATIONS

International Search Report for PCT/EP2014/063319 mailed Sep. 9, 2014, four pages.
Written Opinion of the ISA for PCT/EP2014/063319 mailed Sep. 9, 2014, five pages.

\* cited by examiner

*Primary Examiner* — Yate K Cutliff
(74) *Attorney, Agent, or Firm* — Nixon & Vanderhye P.C.

(57) ABSTRACT

The present invention relates to a novel method for producing 2-(4-N,N-dialkylamino-2-hydroxybenzoyl) benzoates.

21 Claims, No Drawings

METHOD FOR PRODUCING 2-(4-N,N-DIALKYLAMINO-2-HYDROXYBENZOYL) BENZOATES

This application is the U.S. national phase of International Application No. PCT/EP2014/063319 filed 25 Jun. 2014 which designated the U.S. and claims priority to International Application No. PCT/CN2013/000772 filed 27 Jun. 2013, the entire contents of each of which are hereby incorporated by reference.

The present invention relates to a novel method for producing 2-(4-N,N-dialkylamino-2-hydroxybenzoyl) benzoates.

Sun care products have evolved considerably over the years. Earlier formulations were intended to protect the user from UV-B radiation (UVB) as was once thought that UV-B rays were the most important contributors to wrinkling, skin disease, and skin cancer. However, more recent studies have shown that UV-A radiation (UVA) is equally or even more important in the development of solar damage and skin diseases, such as lupus erythematosus and melanoma and non-melanoma skin cancers. Thus, today's focus is toward eliminating as much of UVA (320-400 nm) and/or UVB (280-320 nm) light as possible.

It is well known to a person skilled in the art that substances which have a benzophenone structure are characterized by very good absorption properties in the UV-A region. Particular suitable representatives of this class of substance are e.g. 2-(4-N,N-dialkylamino-2-hydroxybenzoyl)benzoic alkyl esters. Their use as photostable UV filters in cosmetic or pharmaceutical preparations is e.g. described in U.S. Pat. No. 6,409,995B1.

Polymeric UV-filter substances carrying such 2-(4-N,N-dialkylamino-2-hydroxybenzoyl)-benzoic alkyl ester residues are also known and e.g. disclosed in EP1 494 642 and WO2011/070068.

The abovementioned 2-(4-N,N-dialkylamino-2-hydroxybenzoyl)benzoic alkyl esters can be prepared by esterification of 2-(4-N,N-dialkylamino-2-hydroxybenzoyl)benzoic acid as e.g. outlined in U.S. Pat. No. 6,409,995B1 or US2005165099A1. However, the 2-(4-N,N-dialkylamino-2-hydroxybenzoyl)benzoic alkyl esters prepared in accordance with the abovementioned processes often exhibit an undesired discoloration and impurity profile and thus do not satisfy the high quality standards which are required of these compounds for use as UV filters in cosmetic preparations or to be coupled to a polymeric backbone. Furthermore, the methods disclosed so far involve elaborate purification steps which are not suitable for large scale production and lead to decreased yields.

Thus, there is an ongoing need for an efficient and economic method to prepare 2-(4-N,N-dialkylamino-2-hydroxybenzoyl)benzoic alkyl esters which do not show a discoloration and exhibit a very low impurity profile.

Surprisingly it has been found that the above mentioned drawbacks can be overcome by applying specific process steps in a consecutive order.

Thus, in one embodiment the invention relates to a method for producing 2-(4-N,N-dialkylamino-2-hydroxybenzoyl) benzoates of formula (I),

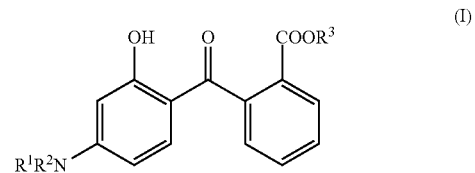

wherein
$R^1$ and $R^2$ are independently of each other $C_1$-$C_6$-alkyl, propargyl or allyl; or
$R^1$ and $R^2$ together with the nitrogen atom they are attached to form a ring with 2-9 carbon atoms; and
$R^3$ is $C_1$-$C_{12}$-alkyl or $C_3$-$C_{10}$-cycloalkyl
characterized in that said method comprises the consecutive steps of
(i) Esterification of 2-(4-N,N-dialkylamino-2-hydroxybenzoyl) benzoic acid of formula (II) by means of a $C_1$-$C_{12}$ alcohol or a cyclic $C_3$-$C_{10}$ alcohol in the presence of an acidic catalyst to obtain 2-(4-N,N-dialkylamino-2-hydroxybenzoyl)benzoate of formula (I):

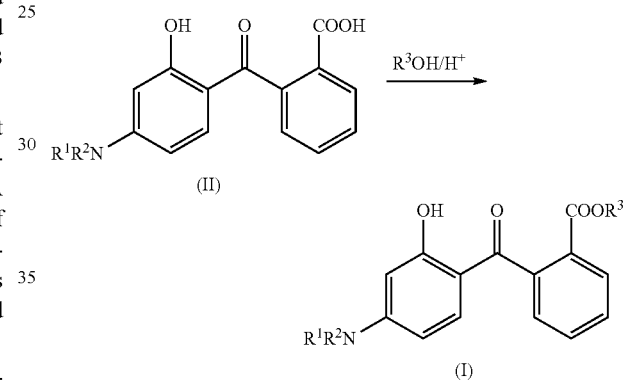

(ii) Dilution of the obtained reaction mixture with an organic solvent and optionally with water,
(iii) Neutralization of the obtained diluted reaction mixture with a suitable base,
(iv) Phase separation of the aqueous phase and the organic solvent phase and
(v) Extraction of the thus obtained organic solvent phase with an aqueous base until the amount of 2-(4-diethylamino-2-hydroxybenzoyl benzoic acid in the organic phase is below 0.1% (as determined by HPLC).

In a further preferred embodiment the process comprises a subsequent filtration step (vi) in which the organic solvent phase, optionally after drying with a suitable drying agent such as e.g. $MgSO_4$ is filtrated through a suitable adsorbent. It is further preferred if the product after the filtration step is precipitated from the organic solvent with a suitable 'precipitation aid' as this further increases the purity and the yield compared to normal crystallization (step (vii)). Optionally, before precipitation, the filtrated organic solvent phase is partially concentrated.

Suitable $C_1$-$C_6$-alkyl radicals which may be mentioned for $R^1$ and $R^2$ are linear or branched $C_1$-$C_6$-alkyl radicals such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methyl-pentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl and 1-ethyl-1-methylpropyl.

When $R^1$ and $R^2$ together with the nitrogen atom they are attached to form a ring, this is preferably a pyrrolidinyl or a piperidinyl ring.

In all embodiments of the present invention preferably, $R^1$ and $R^2$ are the same. More preferably $R^1$ and $R^2$ are linear $C_1$-$C_4$-alkyl radicals, such as most preferably linear $C_1$-$C_3$-alkyl radicals such as in particular methyl and/or ethyl. In all embodiments of the present invention it is particularly preferred if $R^1$ and $R^2$ are both ethyl.

Suitable $C_1$-$C_{12}$-alky radicals which may be mentioned for $R^3$ are linear or branched $C_1$-$C_{12}$-alkyl radicals such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethyl-propyl, 1,2,2-trimethylpropyl, 1-ethyl-1-methylpropyl, 1-ethyl-2-methylpropyl, n-heptyl, 2-ethylhexyl, n-octyl, n-nonyl, n-decyl, n-undecyl and n-dodecyl.

Suitable cycloalkyl radicals which may be mentioned for $R^3$ are preferably linear or branched $C_3$-$C_{10}$-cycloalkyl chains, such as cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl.

In all embodiments of the present invention preferably $R^3$ is a linear or branched $C_1$-$C_8$-alkyl radical, more preferably $R^3$ is a linear $C_1$-$C_6$-alkyl radical, such as in particular a linear $C_1$-$C_3$-alkyl radical such as most in particular methyl or ethyl. Most preferably, in all embodiments of the present invention $R^3$ is methyl.

The esterification of the 2-(4-N,N-dialkylamino-2-hydroxybenzoyl) benzoic acid (II) is generally carried out in a manner known per se (see for this Organikum, VEB Deutscher Verlag der Wissenschaften, Berlin 1986, 16th Edition, pages 400-408) with the corresponding $C_1$-$C_{12}$-alkanols or cyclic $C_3$-$C_{10}$-alkylalcohols in the presence of an acidic catalyst. The alcohol used can function here both as a reagent and as a solvent. To increase the yield, it might be advantageous if the water of reaction formed during the esterification is removed by azeotropic distillation.

Acid catalysts which may be used are, for example, HCl, $H_2SO_4$, $HNO_3$, phosphoric acid, sulfonic acids, such as benzenesulfonic acid, p-toluenesulfonic acid, methanesulfonic acid or mixtures of these acids, but also sulfonic acid group-containing ion exchangers, such as, for example, Lewatits S100 (Bayer). Preferred acidic catalysts are HCl, $H_2SO_4$, methanesulfonic acid and p-toluenesulfonic acid. A particularly preferred embodiment of the process according to the invention involves the esterification being carried out in the presence of sulfuric acid as catalyst.

When the esterification is complete, the reaction mixture is diluted with a suitable organic solvent. Particularly suitable solvents according to the present invention are solvents in which the 2-(4-N,N-dialkylamino-2-hydroxybenzoyl) benzoates of formula (I) is well soluble such as in particular toluene, cyclohexane, ethyl acetate, isopropyl acetate and 1,2-dichloroethane. Preferred organic solvents in all embodiments of the present invention are 1,2-dichloroethane, toluene or cyclohexane. In all embodiments of the present invention the use of toluene as the organic solvent is particularly preferred.

Suitable bases in the neutralization step (iii) are well known to a person skilled in the art and encompass alkali metal carbonates or hydrogen carbonates such as sodium carbonate, sodium hydrogen carbonate, alkali metal hydroxides such as sodium hydroxide and potassium hydroxide as well as ammonia. Particularly suited for the neutralization in step (iii) in all embodiments of the present invention are aqueous solutions of the respective base. Most preferably in all embodiments of the present invention an aqueous solution of sodium hydroxide or an aqueous solution of ammonia (i.e. aqueous ammonium hydroxide) is used.

In case of toluene as organic solvent it is advantageous to use a 7-25 wt.-% aqueous ammonia solution in the neutralization step (iii). In particular a 10-20 wt.-% aqueous ammonia solution, such as most in particular a 12-16 wt.-% aqueous ammonia solution is used as this leads to an optimized amount of solids in the reaction mixture which facilitates the handling.

In the extraction step (v) all solids have to be dissolved before the extraction can take place. This can either be achieved by enlarging the amount of organic solvent—or by increasing the temperature. Preferably the extraction takes place at elevated temperature. The temperature has then to be adjusted according to the organic solvent used and is preferably selected in the range of 20-70° C.

In the case of toluene as organic solvent, the extraction preferably takes place at elevated temperature such as at a temperature selected in the range of 30-70° C. More preferably the temperature is selected in the range of 40-60° C., most preferably in the range of 45-55° C.

Suitable aqueous bases in the extraction step (v) are well known to a person skilled in the art and encompass aqueous solutions of sodium carbonate, sodium hydrogen carbonate, ammonia, alkali metal hydroxides such as sodium hydroxide (NaOH) and potassium hydroxide (KOH). Particularly suited for the extraction step (v) in all embodiments of the present invention are aqueous solutions of NaOH or KOH, such as most preferably an aqueous solution of NaOH as this is particularly suitable to remove residual 2-(4-N,N-dialkylamino-2-hydroxybenzoyl) benzoic acid. The concentration of the base, such as in particular NaOH, in the aqueous solution is preferably selected in the range of 0.5-10 wt.-%, more preferably in the range of 1-5 wt.-% such as e.g. in the range of 2 wt.-%.

In a particular preferred method according to the present invention, in the extraction step (v) the organic solvent is toluene, the aqueous base is an aqueous solution of NaOH at a concentration of 1-5 wt.-% and the extraction is carried out at a temperature selected in the range of 40-60° C., preferably in the range of 45-55° C.

The filtration is performed according to standard methods in the art by placing the adsorbent—optionally wetted by the organic solvent on a suitable filter media and the filtrating the organic solvent phase obtained in step (v)—optionally after a drying and concentration step—through the adsorbent/filter system.

The adsorbents used in the filtration step (vi) are generally solid substances which, due to their large surface area, are able to selectively adsorb impurities from liquid mixtures at their interface. Preference is given to adsorbents chosen from the group consisting of activated carbons, aluminum oxides, zeolites and silica gels. Particularly preferred adsorbents are activated carbons and silica gels. Most preferred is silica gel.

Of the aluminum oxides, basic, neutral or else acidic aluminum oxides may be used. Advantageously, the "active" aluminum oxides, which are obtained, for example, via thermally after-treated aluminum hydroxide gels or by calcination from alpha-aluminum hydroxide, are used.

Of the zeolites, the synthetic zeolites are of particular interest as adsorbent. Details on the composition and structure of these zeolites are given in the CD Rompp Chemie Lexikon—Version 1.0, keyword: zeolites, Stuttgart/New York: Georg Thieme Verlag 1995 and the literature cited therein.

The silica gels suitable as adsorbents are described, inter alia, in the CD Rompp Chemie Lexikon—Version 1.0, keyword: silica gels, Stuttgart/New York: Georg Thieme Verlag 1995 and the literature cited therein. Preferred silica gel in all embodiments of the present invention is 100-200 mesh silica gel e.g. obtainable at Merck Millipore.

The amount of adsorbent used is in the range from 0.1 g to 1 g, preferably 0.25 g to 0.75 g, based in each case on 1 g of the 2-(4-N,N-dialkylamino-2-hydroxybenzoyl) benzoates of formula (I).

In an advantageous embodiment the organic solvent phase used for filtration comprises 2-(4-N,N-dialkylamino-2-hydroxybenzoyl) benzoates of formula (I) in an amount ranging from 50-500 g/l, preferably in the range of 100-350 g/l, most preferably in the range of 200-300 g/l.

After filtration the product is preferably precipitated from the organic solvent phase with a suitable 'precipitation aid'.

The term 'precipitation aid' relates to an organic solvent in which the 2-(4-N,N-Dialkylamino-2-Hydroxybenzoyl) benzoates of formula (I) is hardly soluble (which can easily be determined by a person skilled in the art). Suitable 'precipitation aids' include 2-Methoxy-2-methylpropan (also known as methyl t-butylether (MTBE)), Petroleum ether or n-butanol. Most preferred 'precipitation aid' in all embodiments of the present invention is MTBE.

The ratio (v/v) of the organic solvent phase, preferably after concentration, to the 'precipitation aid' is preferably selected in the range of 5:1 to 1:5, more preferably in the range of 1:1 to 1:3 and most preferably in the range of 1:1.5 to 1:2.5.

A very particularly preferred embodiment the invention relates to a method for producing methyl 2-(4-N,N-diethylamino-2-hydroxybenzoyl) benzoate characterized in that said method comprises the consecutive steps of (i) Esterification of 2-(4-N,N-dialkylamino-2-hydroxybenzoyl) benzoic acid of formula (II) by means of methanol in the presence of an sulfuric acid to obtain methyl 2-(4-N,N-diethylamino-2-hydroxybenzoyl) benzoate,
(ii) Dilution of the obtained reaction mixture with toluene and optionally with water,
(iii) Neutralization of the obtained diluted reaction mixture with an aqueous ammonia solution,
(iv) Phase separation of the aqueous phase and the toluene phase,
(v) Extraction of the thus obtained toluene phase at a temperature of 40-60° C. with an aqueous solution of NaOH until the amount of 2-(4-diethylamino-2-hydroxybenzoyl) benzoic acid in the organic phase is below 0.1% (as determined by HPLC), and optionally drying and concentrating the toluene phase,
(vi) Filtrating the toluene phase through silica gel and
(vii) Isolating the methyl 2-(4-N,N-dialkylamino-2-hydroxybenzoyl) benzoate by precipitation with methyl t-butylether (MTBE).

It is well understood that all preferred embodiments as outlined herein also apply to the specific method outlined above.

The examples below serve to illustrate the process according to the invention in more detail.

EXAMPLE ACCORDING TO INVENTIVE PROCESS 450.0 g 2-(4-diethylamino-2-hydroxybenzoyl) benzoic acid and 912.0 g of methanol were mixed in 5 liter three round flask at room temperature. 546 g of sulfuric acid (98%) was added drop wise in 30 min, and then the reaction mixture was heated to 68° C. After 8 h reflux, the reaction was cooled to room temperature. Two above mentioned batches of reaction mixtures were transferred into the 10 liter jacket reactor, 3600 ml toluene was added into the reactor and cooled. At 15° C., 2000 ml of aqueous ammonia solution (14 wt.-%) was dropped into the reactor in 40 min; after addition a suspension was formed. 1000 ml water was added into the mixture, and then the suspension was heated to 50° C. All solids were dissolved; two clear phase separation system was obtained. After separation, the water phase was extracted with toluene 1500 ml. The organics were combined, then washed with 2% sodium hydroxide (1400 ml*2), (organic layer was monitored with HPLC, until 2-(4-diethylamino-2-hydroxybenzoyl) benzoic acid is below 0.1%); and water (1400 ml*3) to adjust pH to 7.0-7.5. The neutral dark red organic solution was filtered through the glass funnel with 500 g silica gel (100-200 mesh) for decolorization, and the silica gel layer was washed with hot toluene (500 ml*4) to give clear yellow solution. The combined clear yellow toluene solution obtained was transferred into the jacket reactor. Toluene was distilled off at 300 mbar/50° C. When the residual volume was approx. 2000 ml, the distillation was stopped and 4000 ml of methyl t-butyl ether was dropped into the flask slowly and a white precipitate appeared. The resulting suspension was stirred for 20 min and then cooled to 5° C. for 0.5 hours. After filtration, the cake was washed with methyl t-butyl ether (850 ml*2), and the white powder obtained was dried in vacuum box at 45° C. at 2-3 mbar for 20 h yielding 776.8 g (yield: 84%) of 2-(4-diethylamino-2-hydroxybenzoyl) methyl benzoate as white powder with a purity of 99.3% (214 nm area %, ESTD quantitative HPLC analysis).

COMPARATIVE EXAMPLE 150 g (0.48 mol) 2-(4-diethylamino-2-hydroxybenzoyl) benzoic acid and 960 g of methanol were mixed in 5 liter three round flask at room temperature. Afterwards 77 ml of sulfuric acid (98%) was added drop wise, and then the reaction mixture was heated to 68° C. After 18 h, the reaction was cooled to room temperature and neutralized with crystalline sodium hydrogencarbonate (pH=7.5) under significant gas release. The suspension was subsequently mixed with 500 ml of water under stirring stirred and filtered. The filter cake was washed several times with water and then taken up in 2 l of ethyl acetate. The suspension was heated to reflux and filtered again. The filtrate was concentrated to a volume of approximately 1.2 l. The suspension was heated again and decolorized with 10 g of silica gel (100-200 mesh). The hot black solution is filtered through 7 cm of silica gel (100-200 mesh) and washed with 3 l of ethyl acetate. The grey suspension is heated to reflux. The resulting suspension is cooled to 5° C. The crystals were filtered off and washed with diisopropylether and pentane and dried in vacuum box at 45° C. at 2-3 mbar for 20 h yielding 115.35 g (yield: 74%) of 2-(4-diethylamino-2-hydroxybenzoyl) methyl benzoate as gray powder with a purity of 98.0% (214 nm area %, ESTD quantitative HPLC analysis).

The invention claimed is:

1. A method for producing a benzoate compound of formula (I);

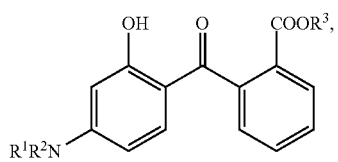

wherein
$R^1$ and $R^2$ are $C_1$-$C_6$-alkyl, propargyl or allyl; or
$R^1$ and $R^2$ together with the nitrogen atom are attached to form a ring with 2-9 carbon atoms; and
$R^3$ is $C_1$-$C_{12}$-alkyl or $C_3$-$C_{10}$-cycloalkyl, wherein
the method comprises the consecutive steps of:
(i) conducting esterification of a benzoic acid compound of formula (II) by means of a $C_1$-$C_{12}$ alcohol or a cyclic $C_3$-$C_{10}$ alcohol in the presence of an acidic catalyst to obtain a reaction mixture comprising the benzoate compound of formula (I):

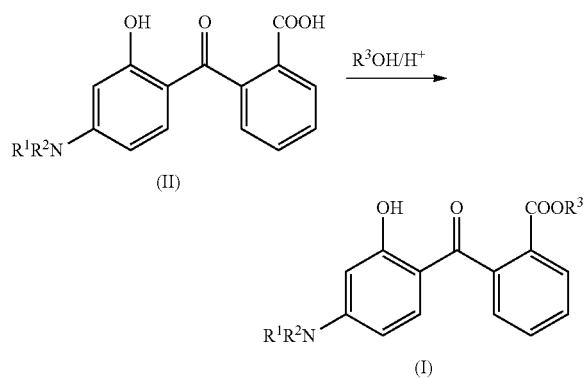

(ii) forming a diluted reaction mixture by diluting the reaction mixture obtained in step (i) with an organic solvent and optionally with water,
(iii) neutralizing the diluted reaction mixture obtained in step (ii) with an aqueous base to form a diluted neutralized reaction mixture comprising an aqueous phase and an organic solvent phase,
(iv) conducting phase separation of the aqueous phase and the organic solvent phase,
(v) extracting the organic solvent phase separated according to step (iv) with an aqueous base until an amount of the benzoic acid compound according to formula (II) in the organic solvent phase is below 0.1%, and
(vi) filtering the organic solvent phase through an adsorbent.

2. The method according to claim 1, wherein $R^1$ and $R^2$ are linear $C_1$-$C_3$-alkyl radicals.

3. The method according to claim 1, wherein $R^3$ is a linear $C_1$-$C_6$-alkyl radical.

4. The method according to claim 1 wherein $R^1$ and $R^2$ are ethyl and $R^3$ is methyl.

5. The method according to claim 1, wherein the organic solvent is toluene.

6. The method according to claim 5, wherein the extraction of step (v) is carried out at a temperature which is in a range of 30-70° C.

7. The method according to claim 1, wherein the aqueous base in step (v) is an aqueous NaOH solution.

8. The method according to claim 1, wherein, between the phase separation step (iv) and the filtration step (vi), the process further comprises a step of drying the organic solvent phase with a drying agent.

9. The method according to claim 8, wherein the absorbent is silica gel.

10. The method according to claim 8, wherein the benzoate compound of formula (I) in the organic solvent phase during filtering according to step (vi) is present in a concentration within a range of 50-500 g/l.

11. The method according to claim 8, wherein the adsorbent is present in an amount in a range from 0.1 to 1 g, based on 1 g of the benzoate compound of formula (I).

12. The method according to claim 1, after the filtration step (vi), the process comprises a precipitation step (vii) which comprises precipitating the benzoate compound of formula (I) from the organic solvent phase with a precipitation aid.

13. The method according to claim 12, wherein a ratio (v/v) of the organic solvent phase to the precipitation aid is in a range of 5:1 to 1:5.

14. The method according to claim 13, wherein the precipitation aid is methyl t butylether.

15. The method according to claim 10, wherein the concentration of the benzoate compound of formula (I) in the organic solvent phase during filtering according to step (vi) is the range of 100-350 g/l.

16. The method according to claim 10, wherein the concentration of the benzoate compound of formula (I) in the organic solvent phase during filtering according to step (vi) is in the range of 200-300 g/l.

17. The method according to claim 11, wherein the adsorbent is present in an amount in the range from 0.25 to 0.75 g, based on 1 g of the benzoate compound of formula (I).

18. The method according to claim 13, wherein the ratio (v/v) of the organic solvent phase to the precipitation aid is in the range of 1:1 to 1:3.

19. The method according to claim 13, wherein the ratio (v/v) of the organic solvent phase to the precipitation aid is in the range of 1:1.5 to 1:2.5.

20. A method for producing methyl 2-(4-N,N-diethylamino-2-hydroxybenzoyl) benzoate, wherein the method comprises the consecutive steps of:
(i) conducting esterification of 2-(4-N,N-diethylamino-2-hydroxybenzol) benzoic acid by means of methanol in the presence of sulfuric acid to obtain a reaction mixture comprising methyl 2-(4 N,N-diethylamino-2-hydroxybenzoyl) benzoate,
(ii) forming a diluted reaction mixture by diluting the reaction mixture obtained according to step (i) with toluene and optionally with water,
(iii) neutralizing the diluted reaction mixture with an aqueous ammonia solution to form a neutralized diluted reaction mixture having an aqueous phase and a toluene phase, (iv) conducting phase separation of the aqueous phase and the toluene phase,
(v) extracting of the toluene phase at a temperature of 40-60° C. with an aqueous solution of NaOH until an amount of 2-(4-diethylamino-2-hydroxybenzoyl) benzoic acid in the organic solvent phase is below 0.1%,
(vi) filtering the toluene phase through silica gel, and
(vii) isolating the methyl 2-(4-N,N-diethylamino-2-hydroxybenzol) benzoate by causing precipitation with methyl t-butylether.

21. The method according to claim 20, wherein after the extracting step (v) and before the filtering step (vi) the method further comprises drying and concentrating the toluene phase.

\* \* \* \* \*